United States Patent [19]

Scandella et al.

[11] Patent Number: 5,162,216

[45] Date of Patent: Nov. 10, 1992

[54] HYBRID GENE REGULATORY REGION OPERABLE IN E. COLI

[75] Inventors: Dorothea H. Scandella, Gaithersburg; Keith H. McKenney, Bethesda, both of Md.

[73] Assignee: Enzon Labs Inc., Gaithersburg, Md.

[21] Appl. No.: 546,707

[22] Filed: Jul. 2, 1990

Related U.S. Application Data

[63] Continuation of Ser. No. 237,616, Aug. 25, 1988, abandoned, which is a continuation of Ser. No. 51,175, May 15, 1987, abandoned, which is a continuation of Ser. No. 534,982, Sep. 23, 1983, abandoned.

[51] Int. Cl.$^5$ .............. C12N 15/70; C12N 15/73; C12N 1/21
[52] U.S. Cl. .............. 435/172.3; 435/69.1; 435/252.33; 435/320.1; 536/27; 935/41
[58] Field of Search .............. 435/320.1, 253.33, 172.3, 435/69.1; 536/27; 935/41, 43

[56] References Cited

U.S. PATENT DOCUMENTS 4,551,433 11/1985 DeBoer .............. 435/172.3

FOREIGN PATENT DOCUMENTS 0041767 12/1981 European Pat. Off. .......... 435/172.3
0067540 12/1982 European Pat. Off. .......... 435/172.3

OTHER PUBLICATIONS

Botterman et al. (1987), DNA, vol. 6, pp. 583-591.
Ptashne et al. (1976), Science, vol. 194, pp. 156-161.
Maniatis et al., 1982 *Molecular Cloning: A Laboratory Manual*, Cold Spring Harbor Laboratory pp. 17-21 and 405-406.
Herman A. DeBoer et al., "Construction of a Tandem, trp-lac Promoter and a Hybrid trp-lac Promoter," *Promoters Structure and Function*, 1982, Eds., Rodriguez et al.

*Primary Examiner*—Richard A. Schwartz
*Assistant Examiner*—Richard M. Lebovitz
*Attorney, Agent, or Firm*—Sterne, Kessler, Goldstein & Fox

[57] ABSTRACT

This invention is directed to a novel hybrid regulatory region for directing and regulating transcription and translation of a gene sequence positioned downstream from the hybrid regulatory region. This hybrid regulatory region includes the promoter sequence of the phage lambda $P_R$ promoter-operator region fused to the operator sequence of the phage lambda $P_L$ promoter-operator region.

14 Claims, 8 Drawing Sheets

HYBRID GENE REGULATORY REGION OPERABLE IN *E. COLI*

This application is a continuation, now abandoned, of application Ser. No. 07/237,616, filed Aug. 25, 1988; which is a continuation of Ser. No. 07/051,175, filed: May 15, 1987; which is a continuation of Ser. No. 06/534,982, Filed: May 23, 1983, now abandoned.

TECHNICAL FIELD

This invention relates to the construction of a regulatory sequence which provides a new operator region to regulate transcription initiation while leaving the promoter intact. This regulatory sequence can be used for the regulated transcription and translation of prokaryotic or eukaryotic genes.

BACKGROUND OF THE INVENTION

The expression of a gene in both prokaryotic and eukaryotic organisms involves first the synthesis of RNA from a DNA template followed by protein synthesis from the RNA.

Transcription, the synthesis of RNA from a DNA template and the first step in the expression of a gene, is controlled by certain signals present on the DNA. These signals are nucleotide sequences which initiate transcription and control the amount of transcription taking place at a given time. The control signals generally consist of promoter and operator regions. The promoter region is a site that is specific for the binding of RNA polymerase and is the initiation point for transcription. Operators function in conjunction with a repressor to control the amount of transcription.

Transcription of a DNA segment is effected by the enzyme RNA polymerase. After RNA polymerase binds to the promoter at the -35 and -10 recognition regions (M. Rosenberg and D. Court, *Ann. Rev. Genet.* 13:319-353, 1979), it transcribes nucleotides which encode a ribosome binding site and translation initiation signal and then transcribes the nucleotides which encode the actual structural gene until it reaches so-called stop signals at the end of the structural gene. The RNA polymerase acts by moving along the DNA segment and synthesizing single-stranded messenger RNA (mRNA) complementary to the DNA. As the mRNA is produced, it is bound by ribosomes at the ribosome binding site (also called the Shine-Dalgarno region). The ribosomes translate the mRNA, beginning at the translation initiation signal and ending at the stop signals, to produce a polypeptide having the amino acid sequence encoded by the DNA.

Through the use of genetic engineering techniques genes from one organism can be removed from that organism and spliced into the genetic information of a second organism and the polypeptide encoded by that gene expressed by the second organism. It is desirous to maximize the expression of the foreign gene and thus obtain high yields of the resultant polypeptide. It has been realized that one way in which gene expression can be regulated is through selection and manipulation of the control signals discussed above.

There is variation among different promoters in their strength and their ability to be repressed efficiently. A promoter which cannot be repressed easily is of only limited use with genes whose protein product in small amounts is toxic to the cell or inhibits maintenance of the plasmid. In such situations, maximal repression of the genes is needed to assure that the host cell and/or plasmid can grow normally until derepression is desired.

Some promoters also suffer a disadvantage when they are present on multi-copy plasmids in that they cannot be repressed efficiently unless a suitable repressor also is located on that plasmid and thus present in multiple copies.

Such promoters are in contrast to others which can be repressed fully by the amount of repressor made from a single chromosomal gene copy. These promoters, however, may have other drawbacks. They may not, for example, be as strong as other promoters.

Various efforts have been made to manipulate different promoter/operator systems so as to enhance promoter strength or increase efficiency of repression. European Patent Application 067,540 (see also De Boer et al. in "Promoters: Structure and Function," ed. R.L. Rodriguez, M.J. Chamberlin, Praeger, 1982, pp. 462-481), for example, describes and claims a hybrid promoter/operator. This hybrid is constructed by ligating the -10 region of one promoter/operator sequence, capable of being derepressed by induction, downstream from a DNA fragment which comprises the -35 region and 5' flanking region of a second promoter which has a stronger signal sequence than the first promoter/operator sequence. The two DNA fragments are linked at a position between about the -35 and -10 recognition sequences for binding of RNA polymerase to the promoter/operator sequence. The fusion results in an entirely new promoter sequence.

Although such a hybrid promoter/operator can be used advantageously in certain situations, it still may prove to be unsatisfactory in others. For example, although the transcription efficiency of the promoter contributing the -10 region may be enhanced, the promoter may not be regulated as tightly as desired under certain circumstances.

There thus remains a need for a regulatory sequence that has a strong promoter which can be repressed highly efficiently. Accordingly, it is an object of this invention to construct a novel regulatory region having these characteristics. It also is an object of this invention to construct such a regulatory region that can be ligated conveniently to a variety of prokaryotic and eukaryotic genes.

SUMMARY OF THE INVENTION

In accordance with the present invention there is disclosed a hybrid regulatory region which comprises the intact promoter sequence of a first promoter/operator region fused to the operator sequence of a second promoter/operator region wherein the operator sequence of said second promoter-operator region can regulate the promoter from the first region more efficiently than can its native operator sequence.

DETAILED DISCLOSURE OF THE INVENTION

Figure 1:
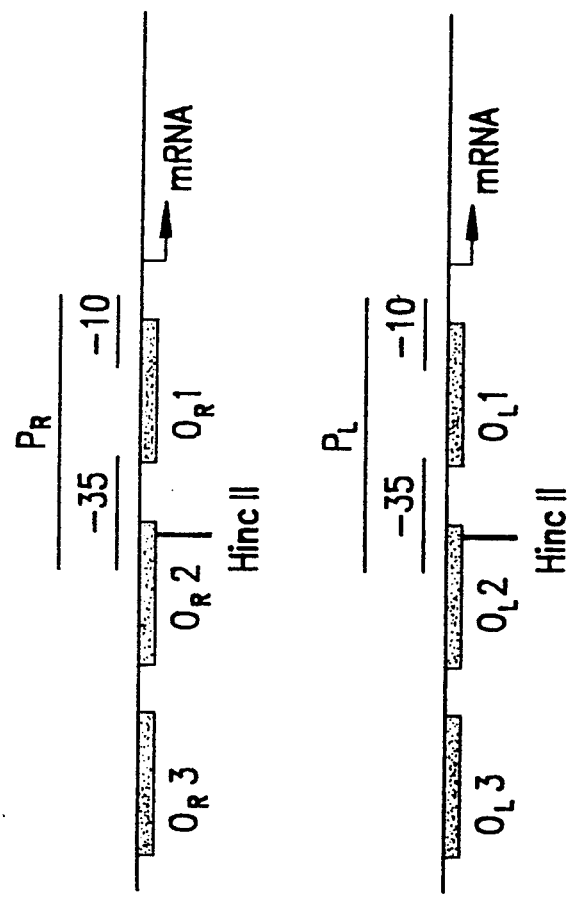
FIG. 1 depicts the promoter/operator sequences which are fused together to make the hybrid $O_L/P_R$ regulatory region.

The present invention relates to a hybrid promoter/operator region capable of directing and regulating transcription of a gene sequence positioned downstream therefrom which provides an intact strong promoter ligated to a new operator region which can regulate transcription initiation more efficiently than the promoter's own natural operator(s). The hybrid regulatory region of this invention is constructed from two promoter/operator regions, a first region which contains a strong promoter and a second region which contains an efficient operator. These regions are cleaved and fragments taken from them are fused together such that the resultant hybrid region comprises the complete promoter sequence of the first region and the efficient operator of the second.

To make this novel hybrid region the first region generally is cleaved at a restriction enzyme recognition site located upstream from the complete promoter sequence and the second region is cleaved at a site downstream from its operator sequence. The appropriate fragments from each of these two regions then are fused together in accordance with conventional methods so as to form the novel hybrid regulatory region of this invention. Alternatively, the first region may be cleaved at a restriction enzyme recognition site that is within the nucleotide sequence of the promoter provided that when the resulting fragment containing the partial sequence of the promoter is fused to the operator sequence of the second region, the nucleotide sequence at the 3' end of the operator region is such that the complete nucleotide sequence for the promoter will be restored.

The two regions may be cut at a naturally occurring common or complementary restriction enzyme recognition site or at a common or complementary site which has been introduced into one or both of the regions by in vitro mutagenesis. Alternatively, if the DNA fragments taken from the two regions have noncomplementary ends, a synthetic DNA segment which matches the restriction sites of the fragments can be prepared and used to link the two fragments.

The details of this invention will be set forth below in terms of a particular embodiment of this invention. It is to be understood, however, that this is done for illustrative purposes only and is not to be construed as limiting.

In one embodiment of this invention the hybrid regulatory region is constructed from two phage λ promoter/operator regions. These two promoters of phage λ, which function early in λ infection, are known as $P_R$ and $P_L$ (Eisen, H. and M. Ptashne, *The Bacteriophage Lambda*, A.D. Hershey, ed., Cold Spring Harbor Lab, N.Y., 1971, pp. 239-270). The $P_R$ sequence provides a strong promoter, but the promoter cannot be repressed as efficiently (i.e., to as low a level) as λ promoter $P_L$ (Queen, C.J., *Mol. Appl. Genet.* 2: 1-10 (1983)). A second disadvantage of the $P_R$ promoter is that when it is present on multi-copy plasmids it can be repressed efficiently only when a λ repressor also is located on the plasmid and thus in multiple copies. When, however, the λ repressor is also present on the plasmid, complete derepression of λ$P_R$ cannot be achieved efficiently unless the temperature is raised to 42° C. In contrast, the $P_L$ promoter can be repressed fully by the amount of repressor made from a single chromosomal gene copy, and derepression is effective at 37°-38° C. The lower induction temperature is useful for proteins which may be rendered less active by heating at 42° C.

The structure of two segments of the λ genome containing promoters $P_R$ and $P_L$ is diagrammed in FIG. 1. RNA polymerase binds to each promoter at the -35 and -10 regions (Rosenberg, M. et al., *Ann. Rev. Genet.* 31: 319-353 (1979); Hawley, D.K. et al., *Nucl Acids Res.* 11: 2237-2255 (1983)). The ability of RNA polymerase to bind each promoter is antagonized by the λ repressor (cI protein) which binds at operator sites $O_L$ 1, 2 and 3 and $O_R$ 1, 2 and 3 (Ptashne, M. et al., Cell 19 :1-11 (1980)).

As shown in FIG. 1, the $P_L$ and $P_R$ regions have a naturally occurring common HincII site. The regions are cut with endonuclease HincII, then a fragment from each region is fused together, such that the sequence upstream from the HincII site (to the left of HincII in FIG. I) is the $P_L$ fragment and the sequence downstream from the HincII site (to the right of HincII in FIG. I) is the $P_R$ fragment. The hybrid region has been designated $O_L/P_R$.

The HincII site in $P_L$ and $P_R$ is located within the -35 region of each promoter. When the $P_L$ and $P_R$ segments are fused at the HincII site, the new regulatory region recreates the exact and complete sequence of $P_R$, for the bases upstream of the HincII cut site are identical in $P_L$ and $P_R$ (Rosenberg et al., supra; Hawley et al; supra).

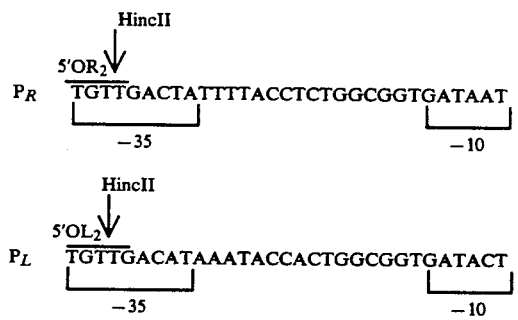

Similarly, the fusion at the HincII site recreates $O_L2$, a portion of which is shown above, because the G residue in $O_L2$ to the right of HincII is also found in $O_R2$. The $O_L/P_R$ hybrid has the repressor binding characteristics of $P_L$. The primary repressor binding sites $O_R1$ and $O_L1$ do not have identical DNA sequences (Pirrotta, V. *Nature* 254:114 (1975); Humayun, et al., *J. Molec. Biol.* 112: 267 (1977)); thus, the differences between $P_R$ and $P_L$ in their ability to be repressed apparently resides in the differences between the remaining repressor sites. The $O_L/P_R$ hybrid made in accordance with the above-discussed procedure contains the $O_L2$ and $O_L3$ repressor sites and the repressor binding characteristics of $P_L$. The $O_L/P_R$ hybrid thus can be repressed to the low basal levels of $O_L$. Furthermore, the $O_L/P_R$ regulatory region can be repressed efficiently when the λ repressor gene (cI) is located on the chromosome of the bacterial host and derepressed efficiently at temperatures less than 42° C.

Figure 2:
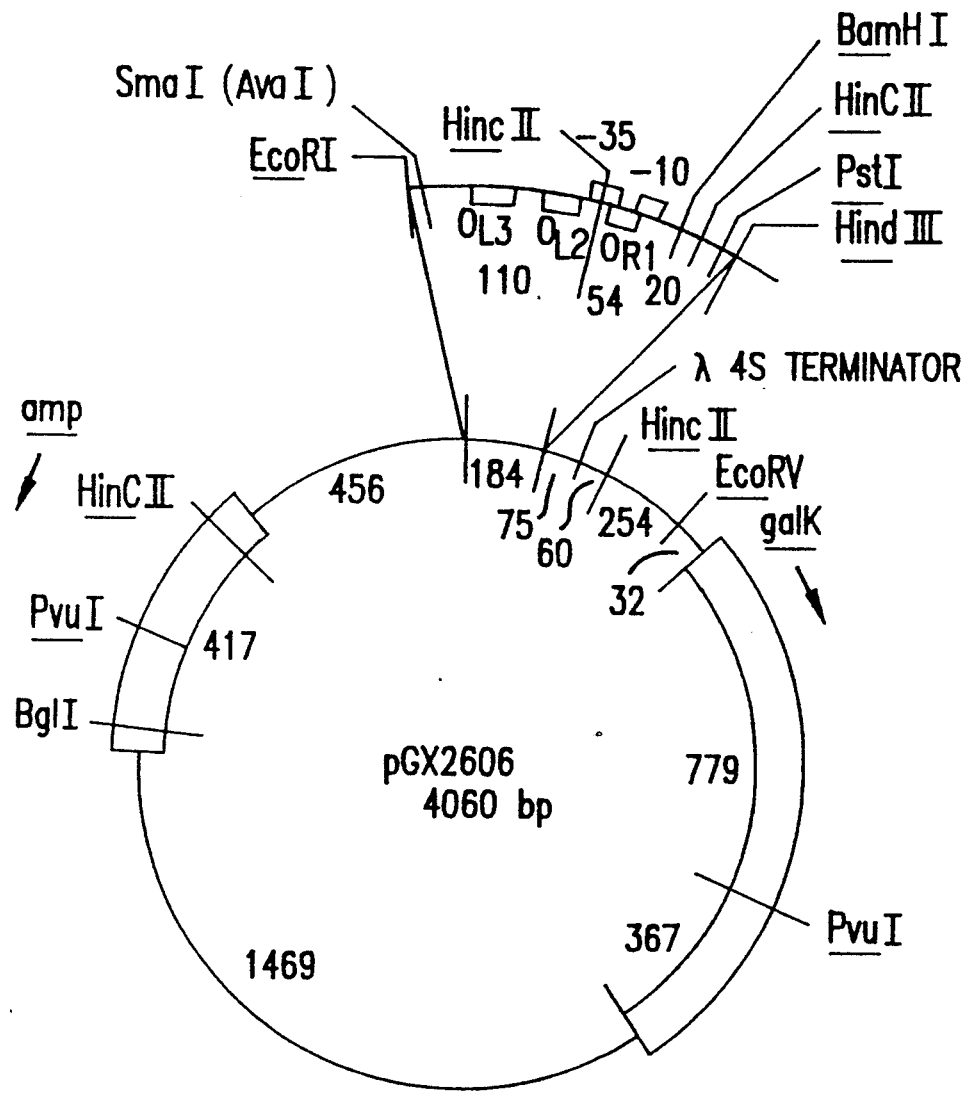
FIG. 2 depicts a map of a plasmid containing the hybrid $O_L/P_R$ regulatory region.

In a specific embodiment of the invention, the $P_L$ fragment is derived from the plasmid pGW7 (provided by Geoffrey Wilson) which contains a segment of the λ genome. The $P_R$ segment is derived from plasmid pCQV2 (Queen, C., *J. Mol. Appl. Genet.* 2:1-10, 1983). pCQV2 contains an alteration in a segment of the λ DNA sequence such that a BamHI site overlaps the ATG of the cro gene, the first gene downstream from $P_R$. When the BamHI site is cleaved and the resulting single stranded region removed, an ATG codon is present at the blunt end of the hybrid promoter/operator region. The resulting $O_L/P_R$ hybrid regulator has been cloned into a plasmid designated pGX2606 (see FIG. 2). An *E.coli* cell culture transformed with this plasmid has been designated GX3123 and deposited with the Northern Regional Research Laboratory, Peoria, Illinois, as NRRL No. B-15551.

In this example, the promoter can be repressed by maintaining the plasmid in an *E.coli* cell which carries the gene for wild type λ repressor on the chromosome. Alternatively, if the plasmid carrying the $O_L/P_R$ region is introduced into a cell which has the gene specifying the temperature-sensitive λ repressor mutant, cI857, repression is maintained at 30° C. Induction of the cI857 lysogen is obtained by raising the temperature to 37°-42° C. expression at a desired time (Campbell, A., *The Bacteriophage Lambda*, ed A.D. Hershey, Cold Spring Harbor Lab, N.Y., 1971, pp. 13-44). Nonregulated expression of the gene of interest linked to $O_L/P_R$ also can be obtained by putting the plasmid into a nonlysogen. With this variation, gene expression is constitutive, and the temperature can be maintained at 37° C. which is the optimal growth temperature for *E.coli*.

The hybrid regulatory region of this invention provides a translation initiation region derived from the region between the promoter and the first gene downstream from the promoter in the plasmid from which it was derived, which can be joined to a gene sequence to provide all needed translation initiation signals for *E.coli*. This includes the ribosome binding site, known as the Shine-Dalgarno region (Shine, J. and L. Dalgarno, *Proc. Natl. Acad. Sci. USA*, 71:1342-46, 1974) and the ATG. As discussed above, for example, the end of the $O_L/P_R$ region proximal to the $P_R$ promoter can be digested so as to provide a blunt end with an ATG (translation initiation codon) at the terminus. The region then can be fused to a gene lacking an ATG.

Alternatively, the region proximal to the 3' end promoter in this hybrid can be altered such that the promoter region no longer carries an ATG codon for translation initiation and so can be fused to genes which carry their own initiation codon. An example of this using the $O_L/P_R$ hybrid is shown by converting the BamHI site to a ClaI site by site directed mutagenesis in vitro (Zoller, M.J., et al. in *Methods in Enzymology* 154:329-350 (1987)).

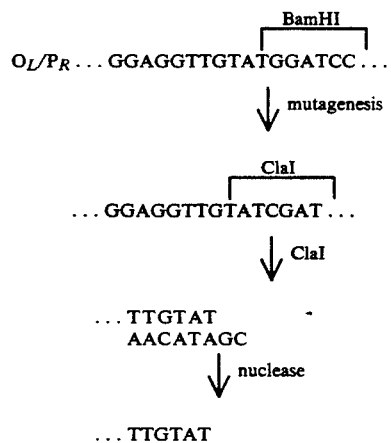

In a third embodiment of this invention, a single base change made with in vitro mutagenesis can be used to create a restriction site downstream from the -10 RNA polymerase recognition site of the hybrid regulatory region. Such a cut separates the hybrid promoter/operator from the Shine/Dalgarno region (Shine, J. and L. Dalgarno, supra, preceding the first downstream gene, thus allowing the insertion of any other natural or synthetic Shine/Dalgarno sequence. These substitutions provide additional possibilities for high expression. One example shows the insertion of an SphI site in the $O_L/P_R$ at such a position by site directed mutagenesis (see above).

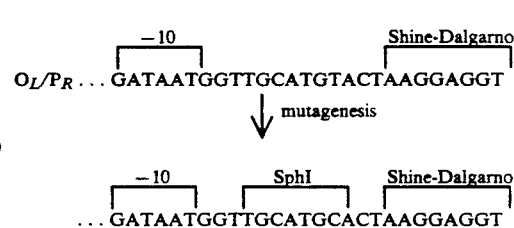

The hybrid promoter/operator regulatory region can be used for transcription and translation of various prokaryotic or eukaryotic genes either in a regulated or an unregulated form. The efficient repression which can be obtained with such a hybrid makes it especially useful for fusion to genes whose protein products are toxic to the cell in small amounts or inhibit plasmid maintenance. Maximal repression of the expression of such genes enables the cells to grow normally and to retain the plasmid until derepression is desired. Expression of the genes then can be induced when cell viability no longer is important.

The following examples are intended to further illustrate this invention and are not to be construed as limiting.

I. Cloning of λ$P_L$ and λ$P_R$ Fragments Into Intermediate Vectors

Figure 3:
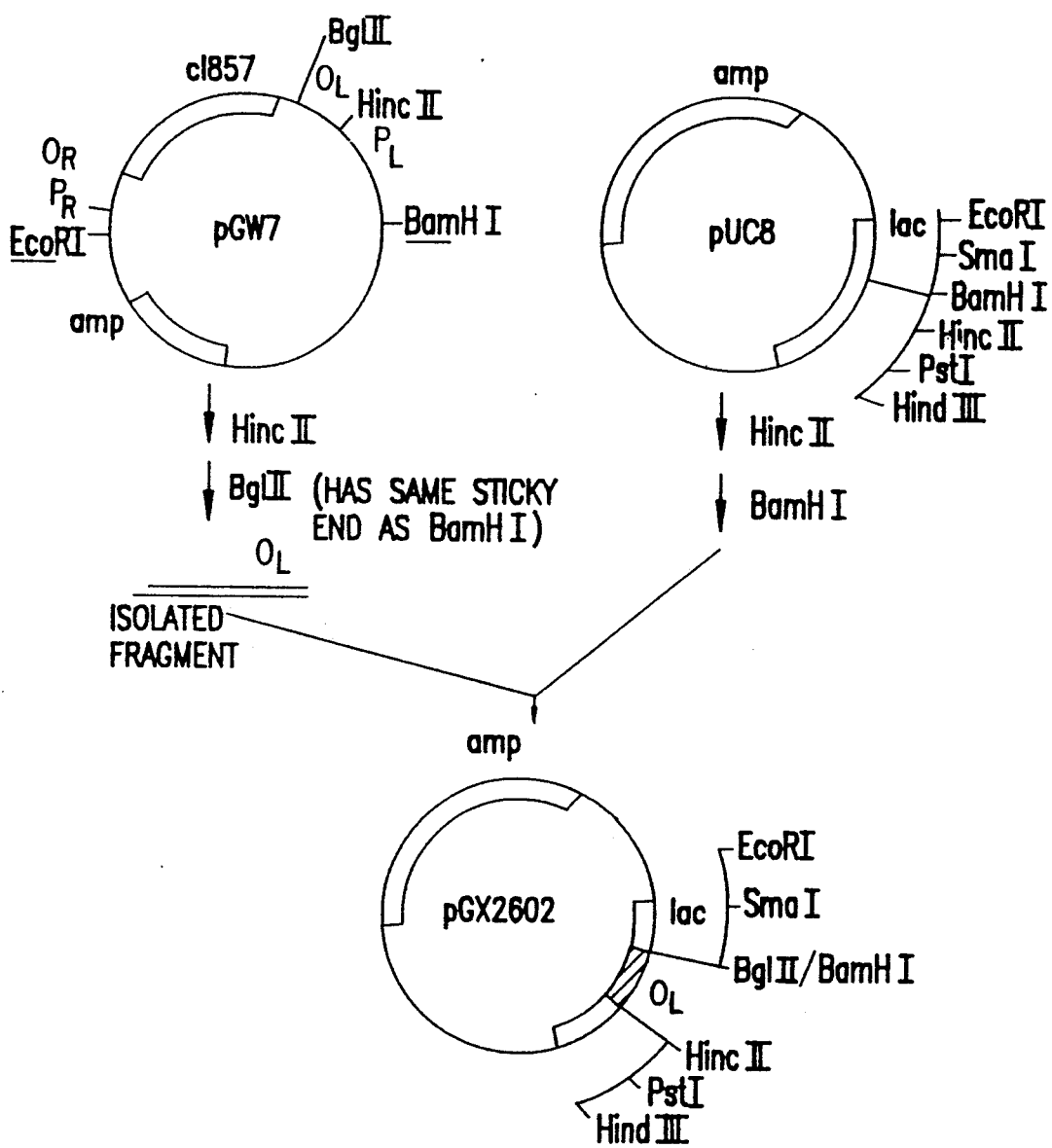
FIGS. 3, 4 and 5 illustrate the steps in the construction of plasmid pGX2606, which contains the $O_L/P_R$ region.

A. Cloning of $P_L$ from PGW7 into pUC8 (FIG. 3)

Plasmid of pGW7 (8007 base pairs, obtained from Geoffrey Wilson) contains a 3987 base pair segment of bacteriophage λ DNA from nucleotides 34498 to 39173 (excluding bases 38104 to 38754 which were deleted). The numbering of the residues in λ DNA is from Sanger, F. et al., *J. Mol. Biol.*, 162, 729-773 (1982). This region contains the early λ promoter $P_L$ from which was isolated a fragment from endonuclease sites BglII to HindII (HincII) (bases 35615 to 35711).

Plasmid pGW7 DNA (10μg) was digested with 11.2 units endonuclease BglII (New England Biolabs, Inc.) for 3 hours at 37° C. in "medium salt" restriction buffer (50mM NaCl, 10mM Tris, pH 7.4, 10mM MgSO4, 1mM dithiothreital). The 5566 base pair fragment was isolated after electrophoresis in a gel of 1% low melting agarose (Bethesda Research Laboratores, Inc.) in E buffer (50 mM Tris, pH 7.5, 30mM sodium acetate, 3mM EDTA) and extracted from the agarose with butanol as described by Langridge et al., *Anal. Biochem.* 103, 264-271 (1980). The DNA was precipitated by addition of 2.5 volumes ethanol and pelleted in an SW40 Beckman ultracentrifuge rotor at 4° C. and 35,000 rpm for 1 hr. The pellet was dried in vacuo and suspended in 200μl H2O.

The isolated 5566 base pair fragment (10μλ) was digested with 8 units endonuclease HindII (Boehringer Mannheim, Gmbh) in medium salt buffer for 20.5 hrs. at 37° C. The digest was extracted with phenol and ether and subjected to electrophoresis on a 6% polyacrylamide gel (acrylamide:bisacrylamide—30:1) in TBE buffer (90 mM Tris, pH 8.3, 90 mM boric acid, 4 mM EDTA). After staining the gel with ethidium bromide, the desired 110 base pair fragment was cut out and removed from the gel by electroelution in 400 μl 0.1X TBE. One ml 0.2M NaCl, 20 mM Tris, pH 7.4, 1mM EDTA was added and the DNA was purified by passage over an Elutip (Schleicher and Schnell, Inc., Keene, N.H.) as suggested by the manufacturer. The DNA was precipitated with ethanol as above and pelleted in a Beckman SW28 ultracentrifuge rotor at 25000 rpm for 1 hr at 4° C. The pellet was dried in vacuo and suspended in 20 μl $H_2O$.

Plasmid pUC8 (Vieira J. and J. Messing. *Gene*, 19 259–268, 1982), 10 μg, was digested with 9.1 units endonuclease Hind II (Boehringer Mannheim, GmbH) for 60 min. at 37° C., then another 9.1 units of enzyme was added and incubated another 15 hrs. at 37° C. The DNA was precipitated in 0.3M sodium acetate, pH 5.5, with 2.5 volume ethanol. The dried pellet was suspended in 16 ml $H_2O$, to which was added medium salt buffer and 20 units endonuclease BamHI in a total reaction volume of 20 μl. The reaction was incubated for 2 hours at 35° C. and then extracted with phenol, precipitated with ethanol, and resuspended in 10 μl $H_2O$.

For ligation of the $P_L$ fragment to pUC8, approximately 5 ng fragment was joined to approximately 30 ng pUC8 in a 20 μl reaction containing 200 units T4 DNA ligase (New England Biolabs, Inc.), 10 μg/ml bovine serum albumin (Bethesda Research Laboratories, Inc.) 0.5mM ATP, 50mM Tris, pH 7.8, 10mM $MgCl_2$, 20 mM dithiothreital. The reaction was carried out for 23 hours at 12° C.

*E.coli* K12 JM103: F' traD36 proA+B+ lacI$^9$ lacZΔM15/Δ(lac pro) supE thi rpsL4 sbcB15 endA) was grown in YT broth (5g yeast extract, 8g trypstone, 5g NaCl per liter $H_2O$) and made competent for transformation by $CaCl_2$ treatment (Cohen, S.N. et al., *Proc. Natl. Acad. Sci USA*, 69, 2110–2114, 1972). Two 200μl samples of competent cells (approx. 2×10$^9$/ml) were each added to 8 μl ligation mix and kept on ice 40 min. The mix was heat shocked at 42° C. 2 min., diluted 15-fold in YT broth, incubated at 37° C. 1 hr., and plated on selective medium (YT broth with 1.5% Difco agar, 2μg/ml ampicillin, 2ml/l 0.1 M isopropylthio-β-D-galactoside [IPTG], 2ml/l 5-bromo-4-chloro-3-indolyl-β-D-galactoside [Xgal]. Ligations which produced plasmids containing the insert were indicated by a color change in the colony in the medium. This method for detecting inserts is described in more detail by Vieira, J. and J. Messing *Gene* 19, 259–269, 1982.

After 15/hrs incubation at 37° C., 85 colonies were obtained. Miniprep DNA was prepared from white colonies by the method of D.S. Holmes and M. Quigley *Anal. Biochem.* 114:193–197 (1981).

To verify that a 96 bp fragment had been inserted into pUC8, miniprep DNA was digested with two endonucleases whose sites border the insert on each side. 0.5 μg DNA in a total volume of 20 μl was incubated with 8 units endonuclease HindIII (Boehringer Mannheim GmbH) in medium salt buffer for 1 hr. at 37° C., then for another 4 hrs at 37° C. with an additional 8 units HindIII. The reaction was stopped by heating for 5 minutes at 65° C. It was brought to 50mMTris, pH 7.4, 100 mM NaCl in a volume of 35 μl and digested further with 20 units endonuclease EcoRI (New England Biolabs, Inc.) for 15 minutes at 37° C. A 5 μl sample was analyzed by electrophoresis on a 5% polyacrylamide gel in TBE buffer. By digesting with EcoRI and HindIII a 118 base pair fragment should be obtained if the correct 96 base pair λ$P_L$ fragment has been inserted between them. The correct isolate was identified as having a fragment which comigrated with a 119 base pair marker. The identity of the insert was confirmed by DNA sequencing (Maxam, A. M. and W. Gilbert *Methods in Enzymology*, ed. L. Grossman, K. Moldave, Academic Press, N.Y. vol. 65, pp. 499–559 (1980)), from DNA which had been extracted from cells by a method similar to the detergent lysis procedure (*Molecular Cloning*, ed. T. Maniatis, E. F. Fritsch, J. Sambrook, Cold Spring Harbor Laboratory, N.Y. p. 92, 1982). The DNA was purified on two CsCl-ethidium bromide gradients by established procedures and passed over a column of Biogel A-50 (BioRad Laboratories).

Figure 4:
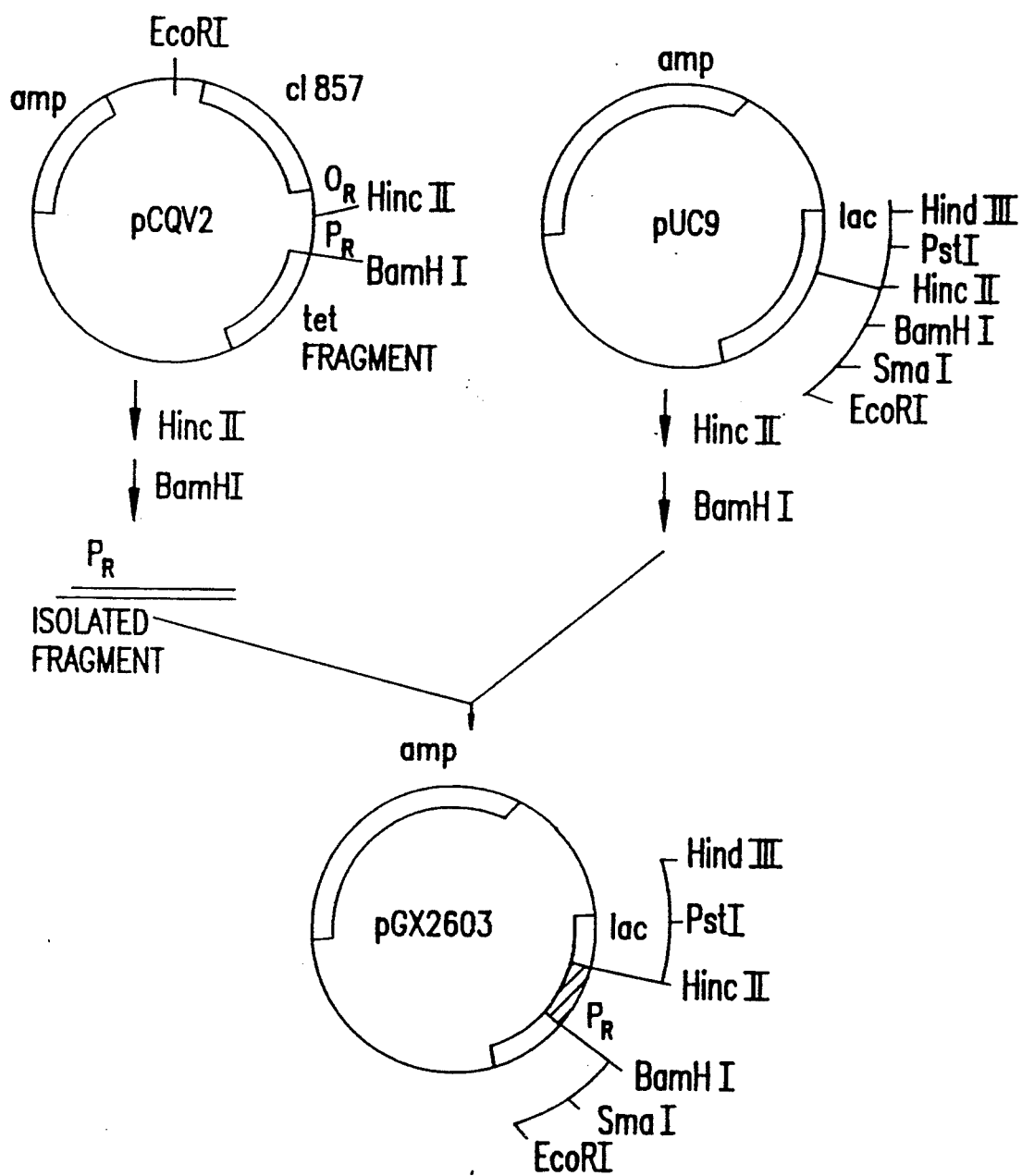

B. Cloning of $P_R$ from pCQV2 into pUC9 (FIG. 4)

These procedures were carried out in a manner analogous to the procedures described in section A; therefore, only specific changes will be noted here. All other details can be assumed to be the same as in section A.

Plasmid pCQV2 (Queen, C. *J. Mol. Appl. Genet.* 2, 1–10, 1983) contains λDNA from base numbers 37169 to 38043 and it was modified to contain an endonuclease BamHI site overlapping the ATG of the λ cro gene. From pCQV2 was isolated a HindIII to BamHI fragment which contains most of $P_R$ and the Shine-Dalgarno region (Shine and Dalgarno, supra) preceding the λ cro gene.

pCQV2 (50 μg) was digested with 50 units endonuclease BamHI (Bethesda Research Laboratories) in medium salt buffer at 37° C. for 1 hr. Endonuclease HindII (Boehringer Mannheim, GmbH) then was added (80 units) and digestion was continued 20.5 hrs. at 37° C. The digest was extracted with phenol and ether and subjected to electrophoresis on a preparative 6% polyacrylamide gel. The 50 base pair BamHI to HindII fragment was removed from the gel by electroelution, passed over a Schleicher and Schuell Elutip and precipitated with ethanol.

The vector pUC9 is similar to pUC8 except that the cloning sites from EcoRI to HindIII are in the opposite orientation (Vieira, J. and J. Messing Gene 19, 259–269, 1982) pUC9 (10μg) was digested with endonuclease BamHI and HindII as described before. Approximately 15 ng digested pUC9 was joined to 0.2 ng $P_R$ fragment in a reaction with 200 units T4 DNA ligase for 23 hrs. at 12° C. in a reaction volume of 20μl.

Competent *E.coli* K12 JM103 cells were transformed with 8μl of the ligation and plated on YT agar plates + IPIG + X-gal + ampicillin at 37° C. After 15 hrs. incubation, there were 326 white colonies. Miniprep DNA was prepared from some of these, and it was digested with EcoRI and HindIII sites on either side of the insert. The insert (50 base pairs) was removed in this way to give a 72 base pair diagnostic fragment. DNA from an isolate with the correct size insert was purified and sequenced by the Maxam-Gilbert technique to confirm its identity.

The cloning of the $P_L$ and $P_R$ fragments into pUC8 and pUC9 resulted in orienting the fragments in the same direction and in placing useful endonuclease sites on either side of the inserts. pUC8 containing $P_L$ is hereafter referred to as pGX2602 and pUC9 containing $P_R$ as pGX2603.

Figure 5:
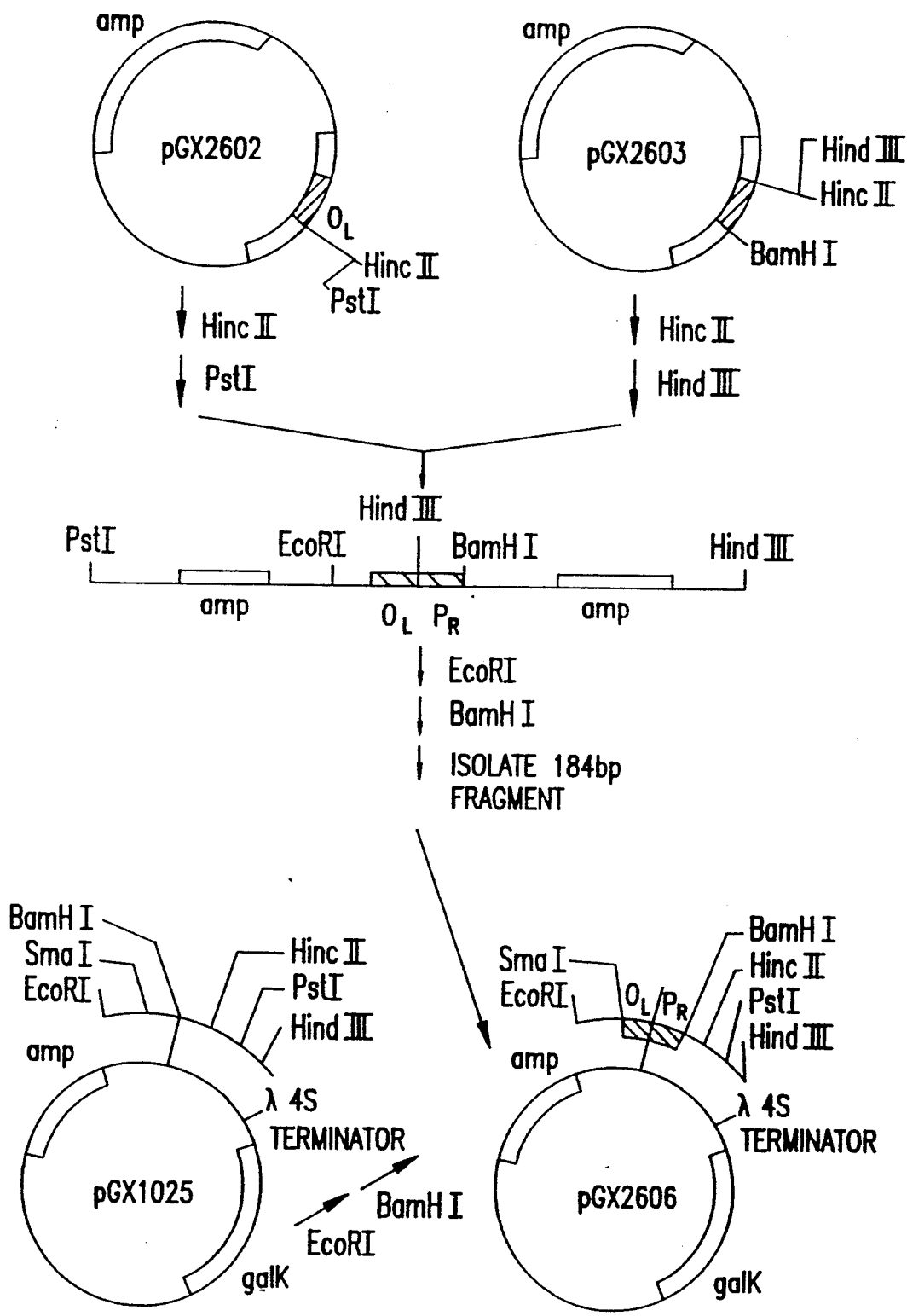

C. Joining of the $P_L$ and $P_R$ Fragments and Cloning of the Joined Piece (FIG. 5)

Purified DNA (25µg each) of pGX2602 and pGX2603 was digested with 24 units of endonuclease HincII (same as HindII, New England Biolabs, Inc.) in medium salt buffer 2 hrs at 37° C.; another 24 units of enzyme were added and incubation continued at 37° C. for 1 hour (pGX2602) or 4 hours (pGX2603). The digested DNAs were precipitated with ethanol and resuspended in medium salt buffer. pGX2602 was then incubated with 56 units endonuclease HindIII (New England Biolabs, Inc.) and pGX2603 was incubated with 25 units endonuclease PstI (Takara Inc., Japan) at 37° C. for 2 hrs. The two DNA samples were then mixed, extracted with phenol, and precipitated with ethanol. The digestion of both DNAs with two different enzymes allowed fewer possible combinations when they were joined in the next step. The desired junction was of $P_L$ to $P_R$ at the HincII site.

For joining of the linearized plasmid, the DNA (50µg) was treated with 2000 units T4 polynucleotide ligase (New England Biolabs, Inc.) in a volume of 100 µl for 15 hr. at 16° C. Another 2000 units of ligase was added and incubation was continued for another 48 hrs.

An EcoRI to BamHI fragment which was thought to contain the left operator fused to $P_R$ was removed from the joined linear DNA fragments and cloned into another plasmid. This was done by first digesting the DNA with 100 units endonuclease EcoRI (New England Biolabs, Inc.) at 37° C. for 2 hrs. and precipitating it with ethanol. The pellet was suspended in 96 µl 100mM Tris, pH 8.0 and digested with 944 units (4 µl) bacterial alkaline phosphatase for 40 min. at 65° C. to remove 5' phosphate groups. After three extractions with phenol and an ethanol precipitation, the free ends were labeled with $\lambda^{32}$P-ATP by incubating in 50 mM Tris, pH 7.4, 10mM MgCl$_2$, 5mM dithiothreital with 10 units T4 polynucleotide kinase (P.L. Biochemicals Inc.) and 100 µCi $^{32}$P-ATP (Amersham, Inc. 6300 Ci/m mol) at 37° C. for 35 min. Unlabeled ATP was added to 1mM and incubated for 10 min at 37° C. The mixture was extracted with phenol, and the DNA was precipitated with ethanol. The DNA was then digested with 80 units endonuclease BamHI in medium salt buffer for 2 hrs. at 37° C., extracted with phenol and precipitated with ethanol. The pellet was suspended in 45 µl TBE + dyes (80% glycerol, 0.5% bromphenol blue, 0.5% xylene cyanol) and loaded onto a 3 mm thick 6% polyacrylamide preparatory gel. The gel was made from 11.2 ml acrylamide (40%; 30:1 acrylamide: bis-acrylamide), 56 ml H$_2$O, 7.5 ml 10X TBE, 0.5ml 10% ammonium persulfate and 55 µl TEMED (BioRad Laboratories, Inc.). After electrophoresis at 250V for 1 hr., the gel was stained with ethidium bromide, and the 150 base pair EcoRI to BamHI fragment was excised, removed from the gel by electroelution, passed over a Schleicher and Schuell Elutip and precipitated with ethanol. The amount of material at this point was barely detectable by ethidium bromide staining, therefore, the fragment was hereafter detected on gels by autoadiography since it was end-labeled with $^{32}$P.

The plasmid pGX1025 was used as the vector for cloning of the $O_L/P_R$ fragment. It was digested with endonucleases EcoRI and BamHI under conditions described previously, and then it was treated with bacterial alkaline phosphatase to remove 5' phosphates and thereby to permit recircularization of the plasmid only when it was joined to the $O_L/P_R$ fragment.

Conditions for ligation of the $O_L/P_R$ fragment to the vector were as follows: 200 units T4 DNA ligase (New England Biolabs), 500 ng pGX1025 prepared as described above and the entire recovered $O_L/P_R$ fragment (amount unknown) under standard reaction conditions and a 20 µl total volume. Incubation was at 16° C. for 18 hrs.

The host for transformation of the ligated DNA was *E.coli* K12 JM101(λ) F'traD36 proA+B+ lac19 lacZΔM15/Δ(lac pro) supE thi. Cells (200 µl) were made competent and transformed by 8 µl ligation mixture as described for JM103(λ). The transformed cell suspension was divided into 200 µl aliquots and plated on LB agar (1.0% tryptone, 0.5% yeast extract, 1.5% agar, all from Difco Laboratories, 0.5% NaCl) + 100 µg/ml ampicillin at 37° C. for 15 hrs. Approximately 6000 transformed colonies were obtained.

Miniprep DNA was prepared (Holmes and Quigley, supra) from 64 colonies grown to saturation in 10ml LB (broth minus agar). The plasmid DNA was extracted twice with phenol, precipitated with ethanol, and suspended in 100 µl 10mM Tris, 1mM EDTA, pH 8.0. A sample of each miniprep DNA, 5 µl in a total volume of 20 µl, was digested with 12 units endonuclease HincII (New England Biolabs, Inc.) in medium salt buffer for 2 hrs at 37° C. Two isolates had a diagnostic piece of 50–60 base pairs when the digest was analyzed by electrophoresis on a 5% polyacrylamide minigel. This HincII fragment originated from the HincII site internal to the $O_L/P_R$ fragment and from a HincII site just 3' to the insert in the vector plasmid. Another diagnostic test was to digest 5 µl miniprep DNA with 16 units endonuclease BamHI (New England Biolabs, Inc.) in medium salt buffer for 2 hrs. at 37° C. The completion of the BamHI digestion was confirmed by electrophoresis of a small portion of the digest on a 1% agarose minigel. The digest was then brought to 100mM NaCl, 50 mM Tris, pH 7.4 and digested with 20 units endonuclease EcoRI for 2 hrs at 37° C. The mixture was analyzed by electrophoresis on a 5% polyacrylamide gel. The BamHI and EcoRI sites flank the $O_L/P_R$ insert; therefore, this digestion should yield a fragment of 164bp. The two isolates which had the correct HincII fragment also had the correct BamHI to EcoRI fragment.

In order to confirm the identity of the $O_L/P_R$ insert, DNA was purified from one isolate which had the correct restriction pattern and subjected to DNA sequencing by the technique of Maxam and Gilbert. The sequence was identical to that of the corresponding segments from phage λ (Sanger, F., et al. supra).

The plasmid containing $O_L/P_R$ has been designated pGX2606. An *E.coli* culture transformed with this plasmid has been designated GX3123 and Deposited with the Northern Regional Laboratory as NRRL No. B-15551.

EXAMPLE II

Expression of Human Serum Albumin Gene Under the Control of the $O_L/P_R$ Regulatory Region Insertion of an XhoI Cleavage Site Preceding the Sequence Coding Mature Human Serum Albumin (HSA)

The $O_L/P_R$ hybrid region was used to regulate expression of a human serum albumin (HSA) gene. In this procedure, the $O_L/P_R$ regulatory region supplied the promoter, Shine-Dalgarno region, and ATG codon for translation initiation. The $O_L/P_R$ region was ligated to a mature HSA coding sequence which contained no ATG codon at its 5' end. This form of HSA was created by introducing a restriction site (XhoI) which overlapped the codon for the first amino acid of HSA. Oligonucleotide-directed mutagenesis was used to modify the wild type sequence coding for preproHSA in order to place an XhoI restriction endonuclease cleavage site overlapping the 5' end of the mature HSA coding sequence. The strategy for this mutagensis and for expression of metHSA in *E.coli* from this modified sequence is outlined in the following diagram and described below.

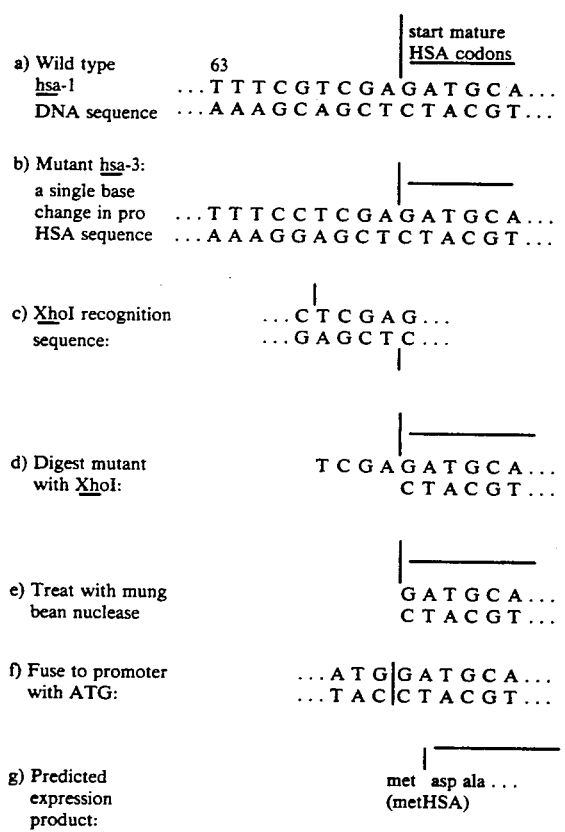

The mutagenesis was accomplished in the following steps, adapted from Zoller, M. and M. Smith (supra).

Figure 6:
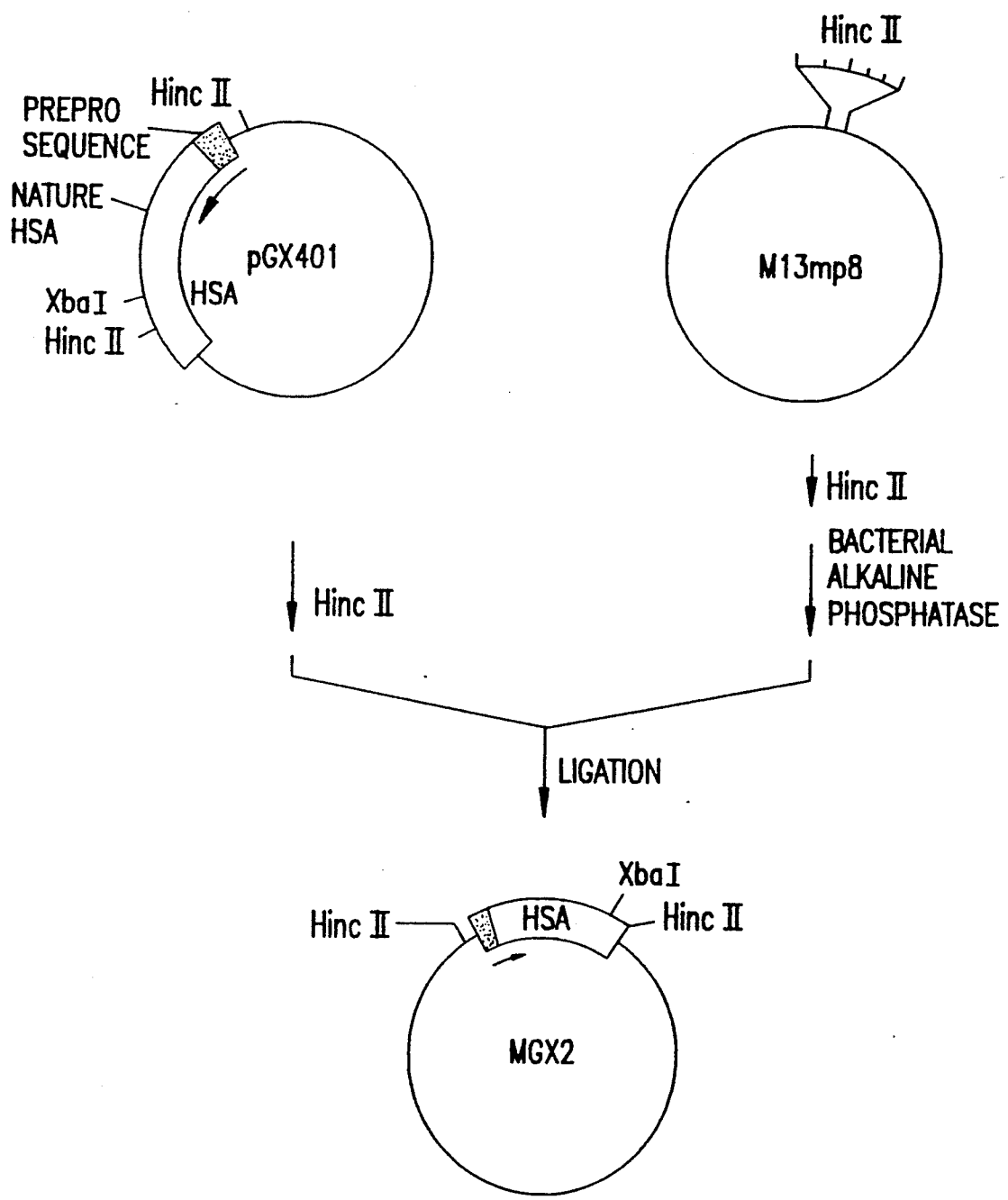
FIGS. 6, 7, and 8 illustrate the steps in the construction of plasmid pGX1043.

1. A portion of a human serum albumin gene was subcloned into the bacteriophage M13mp8, as shown in FIG. 6. Purified DNA from plasmid pGX401, containing a full length HSA clone with pre-pro sequences (designated hsa-1) was digested with HincII and the 1.35 kb fragment comprised of hsa-1 sequences from nucleotides -22 to 1328 was purified by electroelution from an agarose gel. M13mp8 was digested with HincII and treated exhaustively with bacterial alkaline phosphatase (BAP) to remove 5' phosphates. BAP-treated M13mp8 DNA was incubated with the purified hsa-1 HincII fragment in the presence of T4 DNA ligase at 12° C. (1.35:1 molar ratio of vector to insert). The ligation mix was used to transfect *E.coli* strain JM103. The hsa-1 sequence could be inserted into M13mp8 in either clockwise or counterclockwise orientation such that the single-stranded viral DNA from the recombinants would contain either the sense or nonsense strand of hsa-1. To determine the orientation of the insert, plaques were screened by hybridization with oligomer probes complementary to a portion of the sense or nonsense strands of hsa-1 (as described in detail below). An isolate in which the hsa-1 fragment had been inserted in the desired orientation was confirmed by restriction endonuclease mapping and by DNA sequencing from the 3' HincII site toward the XbaI site. The phage containing the cloned hsa-1 fragment was designated MGX-2.

2. The desired mutant differed from the wild type sequence by a single nucleotide. A 17 base oligonucleotide was synthesized which was complementary to the wild type sequence except for a single base mismatch at the position of the desired base change (G→C).

3. The mutagenic oligonucleotide was used as a primer for DNA synthesis with DNA polymerase I. After treatment with DNA ligase the product heteroduplex closed circular DNA molecules were purified by alkaline sucrose gradient centrifugation, pooled, dialyzed, and used to transfect competent *E.coli*.

4. The plaques obtained were screened by hybridization of phage DNA to the mutagenic oligonucleotide. The principle behind this procedure is that the oligonucleotide used to direct the mutagenesis will form a duplex of higher thermal stability with mutant DNA, to which it is perfectly matched (17 of 17 base it is imperfectly matched (16 of 17 base pairs). Therefore the mutant phage can be differentiated from wild type phage in a hybridization experiment under conditions which discriminate between perfectly matched oligomers and mismatched oligomers (R.B. Wallace, M.J. Johnson, T. Hirose, T. Miyake, E.H. Kawashima, and K. Itakura, *Nucl. Acids. Res.* 9:879, 1981). Phage stocks were prepared from individual plagues. 20 μl of each phage supernatant was spotted onto nitrocellulose filter paper using an S & S Minifold ™ device (96 well capacity) to concentrate the 20 μl onto a small area of the filter. Samples were applied in duplicate to make identical 4×12 arrays.

The filter was air dried and baked in vacuo at 80° C. for 2 hours. This filter was prehybridized and then hybridized with 5' end labeled oligomer (10 pmol in 4 ml) as described in Zoller and Smith, supra. After one hour of hybridization at 25° C., the filter was removed from the probe solution and rinsed for 2 minutes in 50 ml 6XSSC at 25° C. The filter was cut horizontally to separate the identical arrays. The top half of the filter was washed at 48° C. for 10 minutes (2X25 ml 6XSSC) and the bottom half at 52° C. for 10 minutes (2X25 ml 6XSSC). Filters were air dried and exposed to X-ray film for 12 hours at room temperature. It was determined that hsa-1 DNA (MGX2) formed mismatched hybrids with the mutagenic oligonucleotide in 1 M salt at 25° C. which were stable during washes at 48° C. but unstable at 52° C. Therefore, duplicate DNA samples from plaques obtained after mutagenesis were hybridized at 25° C. and then were washed at 48° C. and 52° C.

5. Double-stranded replicative form DNA was prepared from two hybridization-positive (A7,D7) and two hybridization-negative (A8,D8) clones. Each DNA was tested for the presence of an XhoI cleavage site. DNA from phages A7 and D7 was cleaved by XhoI; DNA from phages A8 and D8 was not. The correct location of the XhoI site in the DNA from phages A7 and D7 was confirmed by digestion with various other restriction enzymes. DNA sequence analysis confirmed the desired base change had occurred. This variant of hsa is called hsa-3, and the M13 clone bearing it is called MGX4. MGX4 has a restriction site which will cleave precisely at the 5' end of the mature HSA coding sequence.

Reconstruction of hsa-3 in a Plasmid Vector

Figure 7:
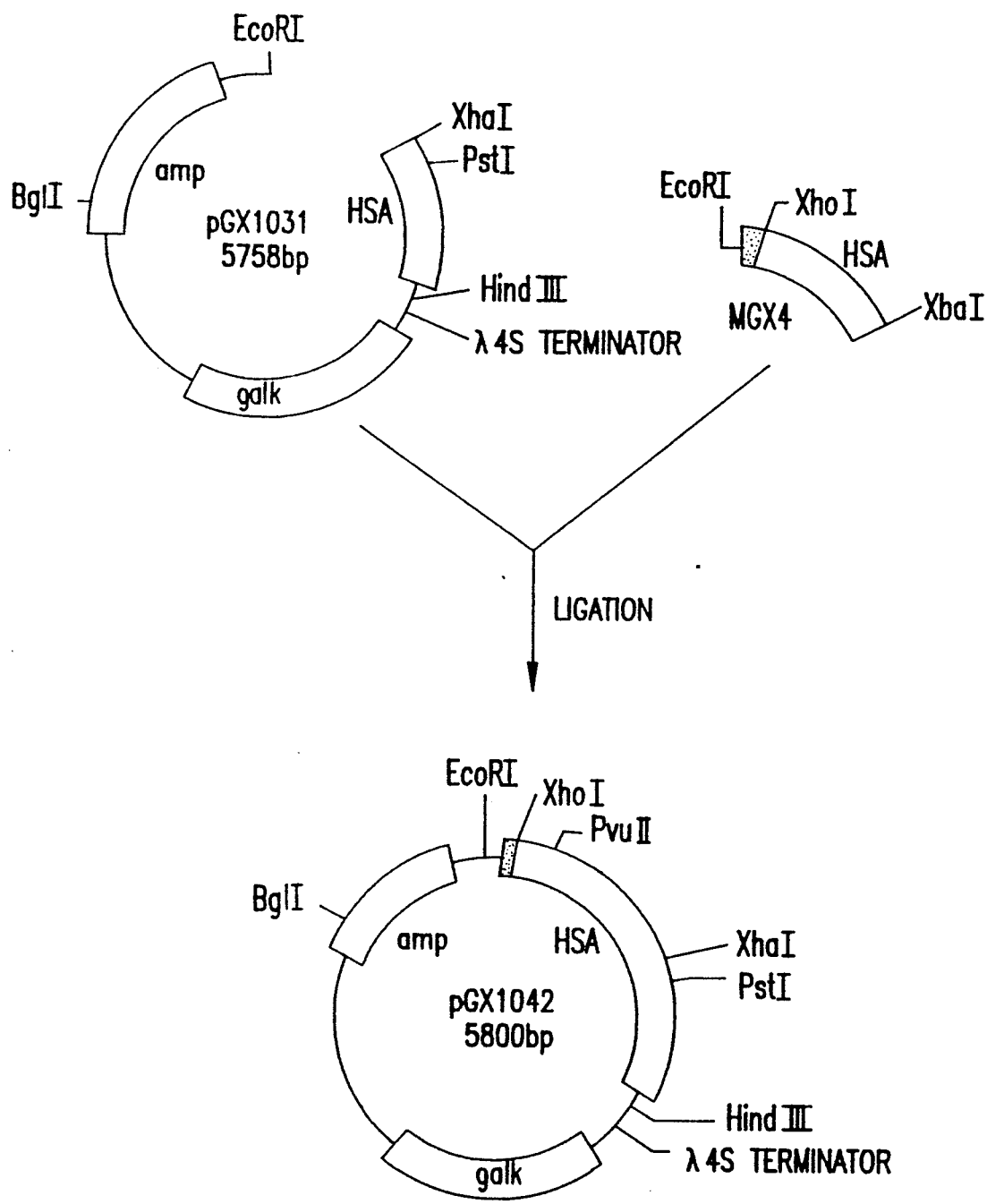

The hsa-3 gene was constructed in a plasmid vector suitable for the addition of expression signals. Plasmid pGX1031 contains all of the hsa-1 clone from pGX401, except a small section of the prepro region (3 codons). It was used to provide the 3' end of the gene and other necessary vector components. FIG. 7 outlines the procedure used to fuse the 5' portion of the hsa-3 gene from MGX4 to the 3' end of the hsa-1 gene in pGX1031 in order to make pGX1042 containing hsa-3 with the XhoI site. pGX1031 (FIG. 7) was cut with EcoRI and XbaI, and the fragment shown was purified. This fragment was mixed with vector MGX4 DNA cut with the same enzymes, and the mixture was incubated with DNA ligase. After transformation of E.coli JM101 with the ligation mixture, 1200 ampicillin resistant transformants were obtained. Plasmid DNA from 45 of these which were randomly chosen was characterized by digestion with several restriction endonucleases, including XhoI. The plasmid designated pGX1042 was determined to have the desired construction.

Figure 8:
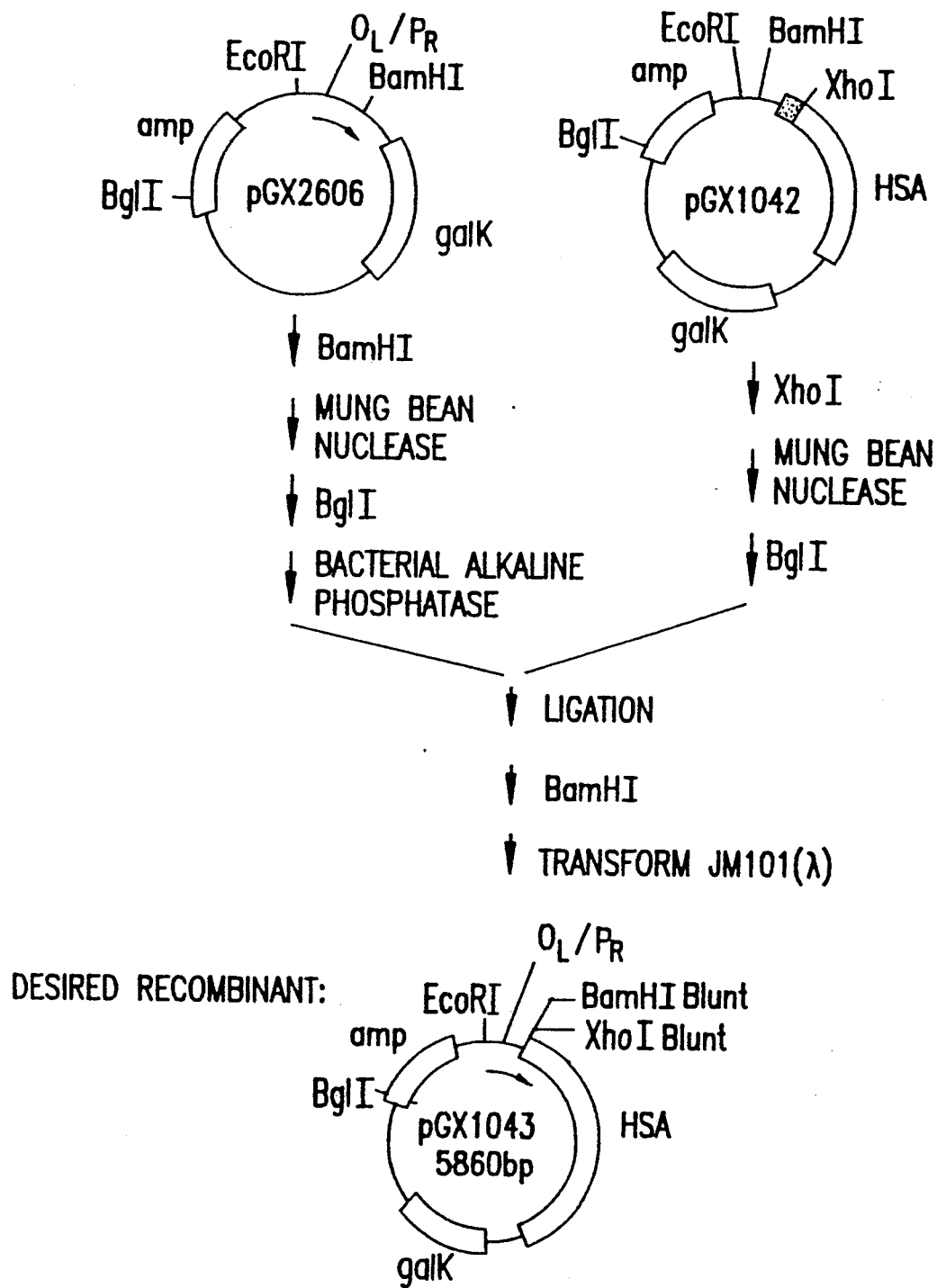

Construction of pGX1043 Containing the OL/PR Regulator Linked to hsa-3 at the XhoI Site The outline for the fusion of $O_L/P_R$ to hsa-3 is shown in FIG. 8. The bacterial host for the transformation was JM101(λ). The $O_L/P_R$ promoter should be repressed in this strain. As fragments for this construction were not purified, the steps described below were performed for reducing the number of parental molecules and one type of recombinant plasmid which otherwise would have been recovered. It thus was expected that the desired transformant would be highly enriched among the colonies recovered.

The following outline illustrates how the junction between the promoter and hsa-3 was made.

were removed by mung bean nuclease, and the plasmid was cut again with BglI. In order to prevent recircularization of pGX2606 in the subsequent ligation, the DNA was treated with bacterial alkaline phosphatase. Plasmid pGX1042 DNA was cut with XhoI, treated with mung bean nuclease to remove the 5' single-stranded ends, and cut with BglI.

Approximately 250 ng of each plasmid DNA was mixed and incubated with T4 DNA ligase at 16° C. for 18 hours. The ligation mixture was cut with BamHI to linearize any pGX1042 plasmid which had recircularized and to linearize one of the possible recombinant types.

Approximately 75 ng of ligated DNA was used to transform competent JM101 (λ). The transformation mixture was plated on medium containing ampicillin and incubated at 37° C. 430 transformants were obtained.

The final plasmid pGX1043 was expected to have the sequence listed (at the bottom of the figure above) at the junction between promoter and hsa-3. The sequence to the left of the arrow including the ATG and the Shine-Dalgarno region (underlined) came from the $O_L/P_R$ segment. The sequence to the right of the arrow came from hsa-3.

The 430 transformants obtained were tested in several ways.

A. Colony hybridization (M. Grunstein and D.S. Hogness *Proc. Natl. Acad. Sci U.S.A.* 72:3961, 1975). A $^{32}$P-labeled probe from the 5' end of hsa was used to detect colonies which carry hsa. The transformants were grown in LB medium plus 100 μg/ml ampicillin in 96 well microtiter plates at 37° C. Aliquots were transferred with a replicator to nitrocellulose filters on LB+ampicillin plates where they were incubated a further 5 hr at 37° C. The conditions processing the filters and doing the hybridization are described in the above reference. The $^{32}$P-labeled DNA probe was prepared from a plasmid containing the sequence for the 5' end of mature HSA. A 178 base pair fragment from the 5' end was labeled with λ-$^{32}$P-ATP using T4 polynucleotide kinase, and purifying the desired hsa fragment on a 5% polyacrylamide gel. Known positive and negative

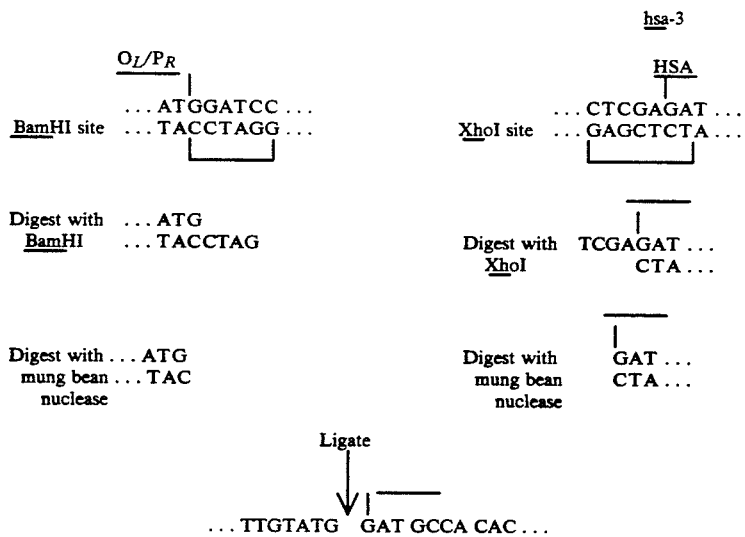

Plasmid pGX2606 DNA was prepared by digestion with BamHI (Rice, R.H. and G.E. Means, *J. Biol. Chem.* 246:831-832 (1971)). The 5' single-stranded ends controls gave the expected results. 39% of the transformants had at least this segment of hsa.

B. *Southern blot* (E.M. Southern, *J. Mol. Biol.* 98: 503, 1975). Since the host cells were lysogenic for λ, the transformants could not be tested directly for the λ $O_L/P_R$ sequence by colony hybridization. Instead, DNA from 45 transformants which did have hsa sequences (identified in step A above) was prepared, plasmid DNA was separated from chromosomal DNA on an agarose gel, and a Southern blot was prepared from this gel. The correct plasmid DNAs were identified by hybridization to a $^{32}$P-labeled $O_L/P_R$ fragment, made by end labeling the 164 base pair EcoRI to BamHI fragment from pGX2606. Hybridization was carried out as in A. 44 isolates had the $O_L/P_R$ sequences.

C. Identification of correctly-constructed plasmid. Plasmid DNAs from each of the 45 transformants tested in step B were analyzed by restriction endonuclease digestion. Two clones appeared to have the proper construction according to: 1) analysis of the size of the undigested plasmids by agarose gel electrophoresis, 2) lack of a BamHI site (the pGX1042 parent has a BamHI site but the desired recombinant does not) and 3) presence of restriction fragments diagnostic for the presence of the $O_L/P_R$ regulator.

D. DNA sequencing. Two of the plasmid DNAs which had all the expected characteristics described above were subject to sequencing in phage M13. M13 subclones of the $O_L/P_R$-hsa-3 fusion from pGX1043 were constructed by cloning the $O_L/P_R$-hsa-3 segment (EcoRI to HindIII) from pGX1043 into M13mp9 (EcoRI to HindIII). Dideoxy DNA sequencing was performed by the method of Sanger, F. et al., *Proc. Natl. Acad. Sci. USA* 74:5463 (1977). An isolate which had the predicted sequence was termed pGX1043.

Expression of metHSA

In order to test for expression of HSA, plasmid pGX1043 was transferred to strain GX1864 which carries the temperature inducible, defective prophage λΔHIΔBam cI857. Transcription was then induced from the $O_L/P_R$ promoter by raising the temperature to 42° C., and samples taken at different times were analyzed. The samples were subjected to electrophoresis in SDS-polyacrylamide gels (U. Laemmli *Nature* 227:6880, 1970) followed by the Western blot procedure (H. Towbin et al. *Proc. Natl. Acad. Sci. U.S.* 76:4350, 1979, W. Burnette *Anal. Biochem.* 112:195, 1981.) HSA was assayed using anti-HSA antibody followed by goat anti-rabbit antibody coupled to horseradish peroxidase. A color development procedure was used to visualize the antigen bands. Controls of the host strain as well as uninduced cells containing pGX1043 showed no stainable bands. Induced pGX1043 DNA gave rise to a major band with a mobility corresponding to a molecular weight of 68 kilodaltons (kd). There were also minor bands with higher mobilities corresponding to lower molecular weights. These minor bands could arise from proteolytic degradation of HSA or from abnormal transcription or translation starts and stops in the hsa gene.

By comparing the intensity of the stained 68kd band from pGx1043 with known amounts of pure HSA (Sigma Chemical Co.), it was estimated that 0.2% of the total protein in extracts of induced pGX1043 was HSA after 2 hours induction. This amount of expression was confirmed by performing immunoprecipitation from extracts labeled with H-leucine during induction as before. Known amounts of HSA (fraction V Sigma Chemical Co.) labeled with $^{14}$C-formaldehyde were used as an internal standard (Rice, R.H. and G.E. Means). The standard was added to cell extracts which were then immunoprecipitated by the method of S.W. Kessler (*J. Immunol.* 115:1617-1624, 1975) with minor modifications. The immunoprecipitate was subjected to electrophoresis on a 7.5% polyacrylamide gel and the HSA band was cut out and ozidized in a Packard sample oxidizer. The $^{14}$C $O_2$ and $^3H_2O$ products were separately quantitated by liquid scintillation spectrometry. The yield of $^3$H-HSA was determined by direct comparison to the yield of added known amounts of HSA-$^{14}$C standard. The amount of $^3$H-HSA was then calculated as a percentage of the total $^3$H leucine incorporated into bacterial protein. The maximum yield of HSA was 0.2% of the total protein.

An *E.coli* culture transformed with this plasmid has been designated GX1864 (pGX1043) and deposited with the Northern Regional Research Labortory, Peoria, Ilinois, as NRRL No. B-15613.

We claim:

1. A recombinant DNA construct comprising a hybrid regulatory region capable of directing and regulating transcription of an operably linked coding sequence, said hybrid regulatory region comprising the $P_R$ promoter sequence and $O_R1$ Operator sequence of the phase lambda $P_R$ promoter-operator region operably linked at the 5' end of said $O_R1$ operator sequence to the 3' end of the $O_L3$-$O_L2$ operator sequence of the phase lambda $P_L$ promoter-operator region.

2. The recombinant DNA construct of claim 1, wherein said $P_R$ promoter sequence and said $O_R1$ operator sequence are fused to said $O_L3$-$O_L2$ operator sequence at the HincII site of said lambda $P_L$ promoter-operator region and the HincII site of said lambda $P_R$ promoter-operator region.

3. A plasmid comprising the recombinant DNA construct of any of claims 1 or 2.

4. A microorganism of the genus and species *E. coli*, transformed with the plasmid of claim 3.

5. The recombinant DNA construct of claims 1 or 2 wherein the 3' terminus of said $P_R$ promoter provides a blunt end with a methionine (ATG) translation initiation codon at said 3' terminus.

6. A plasmid comprising the recombinant DNA construct of claim 2.

7. A microorganism of the genus and species *E. Coli*, transformed with the plasmid of claim 6.

8. The recombinant DNA construct of claims 1 or 2 wherein the 3' terminus of said $P_R$ promoter lacks an ATG codon at said 3' terminus.

9. A plasmid comprising the recombinant DNA construct of claim 8.

10. A microorganism of the genus and species *E. Coli*, transformed with the plasmid of claim 9.

11. The recombinant DNA construct of claims 1 or 2 wherein said hybrid regulatory region lacks the native Shine-Dalgarno region from the $P_R$ promoter sequence of said region.

12. A plasmid comprising the recombinant DNA construct of claim 11.

13. A microorganism of the genus and species *E. Coli*, transformed with the plasmid of claim 12.

14. A microorganism of the genus and species *E. coli*, designated as GX 3123 and deposited with the Northern Regional Laboratory as NRL No. B-15551.

* * * * *